(12) United States Patent
Lindgren

(10) Patent No.: US 9,265,659 B2
(45) Date of Patent: Feb. 23, 2016

(54) EXPANDED METAL AND PROCESS OF MAKING THE SAME

(75) Inventor: Mats Lindgren, Vikmanshyttan (SE)

(73) Assignee: AB KOMPOSITPRODUKTER, Vikmanshyttan (SE)

( * ) Notice: Subject to any disclaimer, the term of this patent is extended or adjusted under 35 U.S.C. 154(b) by 0 days.

(21) Appl. No.: 13/375,092

(22) PCT Filed: Jun. 2, 2010

(86) PCT No.: PCT/SE2010/050607
§ 371 (c)(1),
(2), (4) Date: Nov. 29, 2011

(87) PCT Pub. No.: WO2010/140966
PCT Pub. Date: Dec. 9, 2010

(65) Prior Publication Data
US 2012/0066808 A1    Mar. 22, 2012

(30) Foreign Application Priority Data
Jun. 2, 2009 (SE) ...................................... 0900756

(51) Int. Cl.
| | | |
|---|---|---|
| *B01D 39/12* | (2006.01) | |
| *A61F 9/04* | (2006.01) | |
| *B01D 39/10* | (2006.01) | |
| *A42B 3/22* | (2006.01) | |
| *B21D 31/04* | (2006.01) | |

(52) U.S. Cl.
CPC . *A61F 9/045* (2013.01); *A42B 3/22* (2013.01); *B01D 39/10* (2013.01); *B01D 39/12* (2013.01); *B21D 31/043* (2013.01)

(58) Field of Classification Search
CPC ............................... B01D 39/12; B01D 39/10
USPC ................ 2/9, 410, 5, 175.1, 195.1, 6.3, 171, 2/195.2, 195.3, 195.4, 195.5, 195.6, 207, 2/209.7; 29/6.1; 55/525
See application file for complete search history.

(56) References Cited

U.S. PATENT DOCUMENTS

| | | | | |
|---|---|---|---|---|
| 1,576,121 | A * | 3/1926 | Jarvis ............................... | 55/489 |
| 2,602,521 | A * | 7/1952 | Smith .............................. | 55/487 |
| 3,169,251 | A * | 2/1965 | Humes, Jr. .................... | 2/171.03 |
| 3,308,597 | A * | 3/1967 | Simonton ....................... | 52/635 |

(Continued)

FOREIGN PATENT DOCUMENTS

| | | |
|---|---|---|
| EP | 0689812 A2 | 1/1996 |
| EP | 1160026 A2 | 12/2001 |

(Continued)

*Primary Examiner* — Khaled Annis
(74) *Attorney, Agent, or Firm* — Myers Bigel & Sibley, PA

(57) ABSTRACT

Visor comprising a network structure formed of expanded metal, which network structure has a general extension plane (113, 114, 213, 214) and is formed of wire portions (11, 111, 211) and connecting portions (12, 112, 212), the respective ends of four wire portions (11, 111, 211) being joined in each connecting portion (12, 112, 212), and which wire portions (11, 111, 211) have substantially rectangular cross sections having long sides (111A, 211A) and short sides (111B, 211B). The wire portions (11, 111, 211) are arranged such that the long sides (111A, 211A) of their cross sections have a lesser angle to the general extension plane (113, 114, 213, 214) of the network structure than do the short sides (111B, 211B). The invention also relates to a method for use in the production of such a visor.

6 Claims, 3 Drawing Sheets

(56) References Cited

U.S. PATENT DOCUMENTS

| | | | |
|---|---|---|---|
| 4,988,424 A * | 1/1991 | Woodward et al. | 204/192.29 |
| 5,451,307 A * | 9/1995 | Bennett et al. | 204/196.01 |
| 5,500,271 A * | 3/1996 | Pasch et al. | 428/135 |
| 6,156,444 A * | 12/2000 | Smith et al. | 428/596 |
| 6,327,772 B1 * | 12/2001 | Zadno-Azizi et al. | 29/557 |
| 6,629,016 B1 * | 9/2003 | Smith | 700/145 |
| 6,832,393 B2 * | 12/2004 | Folkesson | 2/410 |
| 2009/0031485 A1 * | 2/2009 | Prusinski et al. | 2/424 |

FOREIGN PATENT DOCUMENTS

| | | |
|---|---|---|
| WO | WO 9730606 A1 | 8/1997 |
| WO | WO 0070978 A1 | 11/2000 |

* cited by examiner

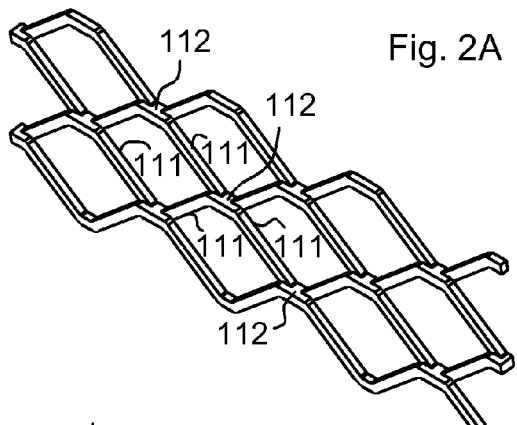
Fig. 2A
Fig. 2B
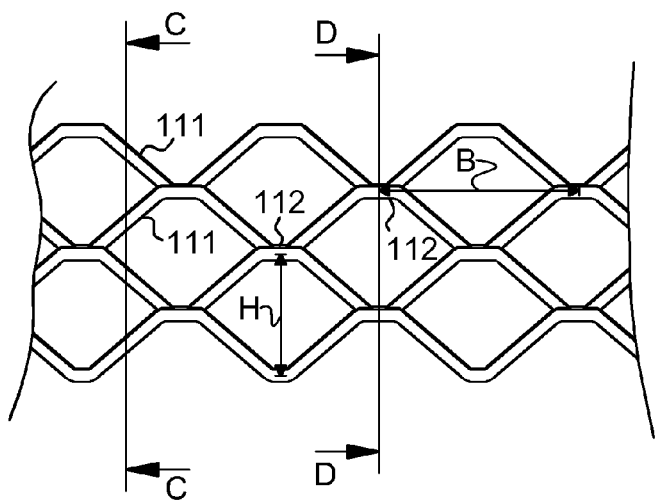
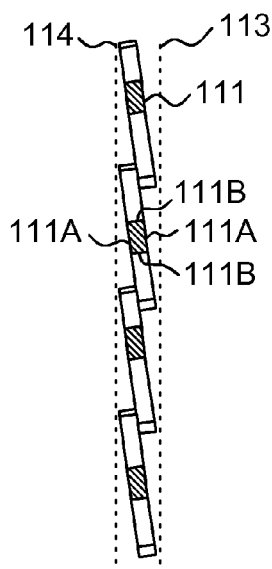
Fig. 2C
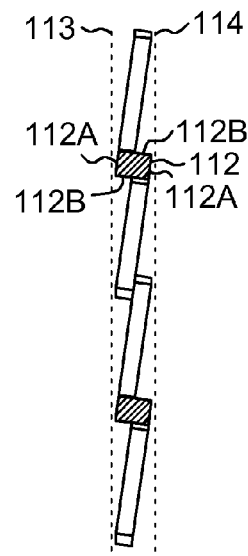
Fig. 2D

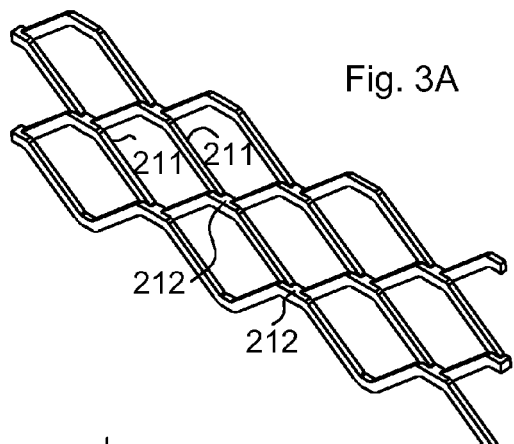
Fig. 3A
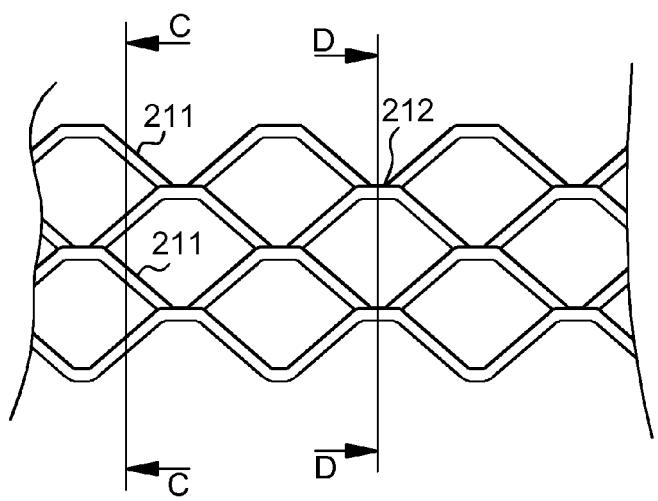
Fig. 3B
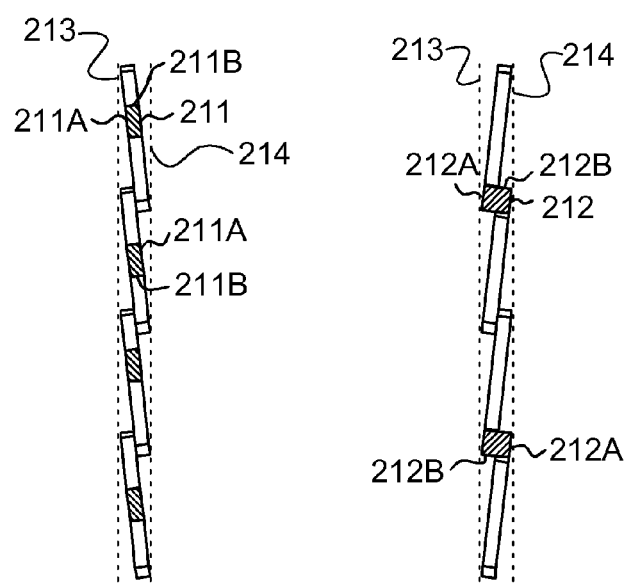
Fig. 3C
Fig. 3D

EXPANDED METAL AND PROCESS OF MAKING THE SAME

RELATED APPLICATIONS

This application is a 35 U.S.C. §371 national phase entry of PCT Application PCT/SE2010/050607, filed Jun. 2, 2010, and published on Dec. 9, 2010, as International Publication No. WO 2010/140966, and which claims the benefit under 35 U.S.C. §119(e) of Swedish Patent Application Serial Number 0900756-8, filed Jun. 2, 2009, the disclosure of each of which is incorporated herein by reference in its entirety.

FIELD OF THE INVENTION

The invention relates to a visor comprising a network structure formed of expanded metal. The invention also relates to a method for the production of such a visor.

BACKGROUND

Visors, sometimes referred to as face shields, are used, for example, in forestry work to protect the face and, in particular, the eyes of the user from particles and small objects which are flying around. The visor is often fixed to a helmet, but can also be arranged on other types of holders, such as, for example, a head band, or the head strap of a pair of earmuffs.

In order not to unnecessarily impair the vision through the visor, they should exhibit high light transmittance. They should also exhibit high strength to prevent particles and objects which hit the visor from penetrating it. Further desirable characteristics are that they do not produce light reflections or other visual disturbances or light distortions, that they prevent an accumulation of condensation and foreign matter, that they are low in weight and that they are easy to clean.

PRIOR ART

Visors which are currently on the market can be divided into three main categories:

Non-latticed transparent visors, which are often formed of a plastics material. These visors give good transparency from the outset and have low weight. However, they often have problems with condensation on the inner side of the visor. Plant parts, resin and other objects which adhere to and are scattered onto the outer side of the visor can be difficult to remove. This substantially impairs the level of vision through the visor and causes repeated work interruptions for cleaning of the visor.

Another type of visor comprises a network structure of separate wires which have been joined together crosswise in junctions. The wires can be formed in plastic or metal and are often joined together by means of glue or lacquer which has been applied over the network structure. In apertured network structures of this kind, the risk of condensation formation and of plant parts, resin or other objects being scattered onto and adhering to the visor is reduced. On the other hand, raindrops tend to adhere in cavities formed at the junctions, which, in rain, makes it necessary to shake the visor repeatedly or otherwise remove the drops. In order to obtain sufficient strength and rigidity, it is further required that the wires have a relatively large cross-sectional dimension, which results in a light transmittance which is impaired to a corresponding degree. A further drawback with this type of visor is that the glue or lacquer at the junctions tends to come loose after a certain period of use. There is hence a risk of the wires sliding apart, so that larger holes than intended are formed between the wires. The risk of objects being able to penetrate the visor is thereby increased.

A third type of visor comprises a network structure having through openings. A network structure has been formed by etching off of material from a thin plate. Such visors can be given a high light transmittance, strength and rigidity. A considerable drawback with the etched visors is, however, the relatively complicated, time-consuming and thus costly production process.

In SE 506 057 C2, it is proposed to produce a visor comprising a latticework, referred to as expanded metal, having two groups of latticed bars, the latticed bars in the one group crossing the latticed bars in the other group. The latticed bars have rectangular or square cross sections. Should the cross sections be rectangular, they are arranged such that the long sides of the cross sections are arranged with a greater angle to the extension plane of the network structure than the angle between the short sides of the cross sections and the extension plane of the network structure. A Venetian blind effect is thereby achieved, which is said to result in the light transmittance for light inciding obliquely from below being considerably better than for light inciding obliquely from above. Vision through the visor at close quarters shall thereby be improved and problems with counter light reduced. In practical use of the visor described in SE 506 057 C2, it has been shown, however, that this Venetian blind effect gives rise to dizziness and nausea in the user.

SUMMARY OF THE INVENTION

One object of the present invention is therefore to provide an improved visor comprising a network structure of expanded metal.

Another object is to provide a visor of this kind which has good light transmittance and transparency and which eliminates or substantially reduces the risk of dizziness, nausea or other complaints for the user.

A further object is to provide a visor of this kind which has good strength and rigidity and which nevertheless has a relatively low weight.

One more object is to provide a visor of this kind which prevents particles, foreign matter or water droplets from adhering to the visor.

Yet another object is to provide a visor of this kind which prevents the formation of light reflections.

Yet another object is to provide a visor of this kind which is easy and relatively cheap to produce.

These and other objects are attained with a visor of the type which is defined in the preamble to Patent Claim 1. The visor exhibits the distinguishing features defined in the characterizing part of the claim.

The visor comprises a network structure which is formed of expanded metal. The network structure has a general extension plane and is formed of wire portions and connecting portions, the respective ends of four wire portions being joined in each connecting portion. The wire portions have substantially rectangular cross sections having long sides and short sides. According to the invention, the wire portions are arranged such that the long sides of their cross sections have a lesser angle to the general extension plane of the network structure than do the short sides.

By virtue of the fact that the visor comprises a network structure of expanded metal, the whole of the network structure is formed in one piece. The problems with sliding-apart wires and remaining water droplets, which occur in network structures formed of joined-together separate wires, are thereby eliminated. Through the use of expanded metal, very good strength and rigidity is also obtained in relation to the quantity of material which forms the network structure. In this way, the open area and thus the light transmittance is kept high, at the same time as high strength and rigidity are maintained. Moreover, the network structure of expanded metal means high productivity and low material consumption, and the production costs can thus be kept relatively low.

In the production of network structures of expanded metal, a metal plate is advanced step by step by a certain specific step width in a feed direction which is parallel with the extension plane of the plate. At one edge of the plate which rests on a support, a toothed punching tool is guided downwards perpendicular to the plate and cuts and also stretches that edge portion of the plate which is placed beyond the support, by a certain distance corresponding to half a mesh height of the finished network structure, perpendicularly down from the unworked plate. After this, the tool is returned to the starting position and the plate is advanced by one more step width. The tool is displaced by a certain distance corresponding to half a mesh width of the finished network structure in the lateral direction, perpendicular to the feed direction of the plate, and is thereafter guided again downwards, cutting and stretching the following edge portion of the plate. Following the next feed step, the tool goes back half a mesh width to the original lateral position and punches again downwards. In this way, a stair-shaped network structure with wire portions which are joined in connecting portions is formed step by step. As a result of the fact that the network structure thereby acquires a general stair shape, the cross sections of the wire portions and of the connecting portions will be tilted in relation to the extension plane of the network structure. The side faces of the wire portions and of the connecting portions are thus not wholly parallel with and perpendicular to the extension plane of the network structure. Instead, the sides of the wire portions and of the connecting portions against which the tool bears, and the sides lying opposite these sides, will acquire a first, greater angle in relation to the extension plane of the network structure. Those sides of the wire portions and of the connecting portions which are perpendicular to these sides acquire a second, lesser angle to the extension plane of the network structure.

According to the invention, the cross sections of the wire portions are rectangular and are arranged such that their long sides constitute those sides of the cross sections which have the lesser angle to the extension plane of the network structure, whilst the short sides of the cross sections have the greater angle to the extension plane of the network structure. This is achieved in the production of the network structure by making the step widths smaller than the plate thickness, in which case the plate thickness will correspond to the length of the long sides of the cross sections, whilst the step width will correspond to the length of the short sides of the cross sections. In practice, the elongation of the wire portions will cause a certain contraction of the cross sections of the wire portions. The length of both the long and the short sides is thus reduced, whilst, at the same time, their mutual length ratio is maintained. In the continued description, for the sake of simplicity, the dimensions of the cross sections of the wire portions are referred to as corresponding to the step width and plate thickness respectively.

It has been shown that such a configuration of the wire portions of the network structure strongly reduces the Venetian blind effect which is found with the previously known visor having a network structure of expanded metal. It has further been shown that the visor according to the invention does not give rise to dizziness, nausea or similar complaints during use.

The length of the short sides of the cross sections of the wire portions expediently constitutes around 55-99% of the length of the long sides. A good light transmittance with no or only slight Venetian blind effect is here obtained, at the same time as the strength and rigidity of the network structure is fully satisfactory. Especially good characteristics are obtained if the length of the short sides constitutes around 60-75% of the length of the long sides.

The network structure is expediently formed of stainless steel, preferably of annealed stainless steel. A visor with good mechanical characteristics is thereby obtained, which is also durable and which advantageously can be used outdoors under arduous weather conditions.

The network structure can be calendered. A stabilization of the shape of the network structure, which makes it easier to handle during production and assembly, is thereby obtained. In the calendering process, the connecting portions, above all, are affected by the calender rolls, since these portions have a greater thickness transversely to the extension plane of the network structure. In the production of the network structure of expanded metal, the width of the connecting portions transversely to the extension plane of the network structure will be constituted by double the wire width in the same direction, which corresponds to two step widths. As for the wire portions, the thickness of the connecting portions perpendicular to the width will correspond to the plate thickness. Hence, according to the invention, a favourable ratio between the width and thickness of the connecting portions is also obtained, which ratio means that the calendering will rotate the connecting portions so that the long side corresponding to the width is straightened up such that it becomes more perpendicular to the extension plane of the network structure. In this way, the exposed surface of the connecting portions parallel with the extension plane of the network structure is reduced, which contributes to a higher total light transmittance through the network structure.

The network structure is expediently heat-treated, for example by heating to 580-640° C. for a suitable dwell time. This produces, firstly, a reduction in deformation stresses which occur in the production of the network structure of expanded metal, whereby the network structure becomes easier to handle during production and assembly. Subjecting of the network structure to a heat treatment allows it to be given very large elongations. It has been shown that the relatively thin plates which are used in the production of the network structure for the visor according to the invention, with a subsequent heat treatment, can be given elongation ratios as large as 1:8. The light transmittance through the network structure is thereby further improved, at the same time as the material consumption can be kept low. As a result of the heat treatment, a further advantage is obtained, in that the surfaces of the network structure are given a darker and matter surface, which considerably reduces the occurrence of light reflections on these surfaces.

The invention also relates to a method for use in production of a visor comprising a network structure of expanded metal. The method according to the invention is defined by the following Patent Claim 6 and is characterized in that the step width is less than the plate thickness, which corresponds to that distinguishing feature of the visor according to the invention which is defined in the characterizing part of Claim 1. Further embodiments of the method are specified in the dependent Claims 7-10. The method according to the invention has corresponding objects and advantages as described above in connection with the summary of the visor according to the invention.

BRIEF DESCRIPTION OF THE FIGURES

Below a detailed description of illustrative embodiments of the invention is given with reference to the drawings, whereof:

FIG. 2A is a perspective view of a part of a network structure belonging to a visor according to a first embodiment of the invention, FIG. 2B is a plan view of the network structure illustrated in FIG. 2A, FIG. 2C is a section along the line C-C in FIG. 2B, FIG. 2D is a section along the line D-D in FIG. 2B, FIGS. 3A-D are views corresponding to those in FIGS. 2A-D, illustrating a network structure belonging to a visor according to another embodiment of the invention.

DETAILED DESCRIPTION OF EMBODIMENTS

Figure 1:
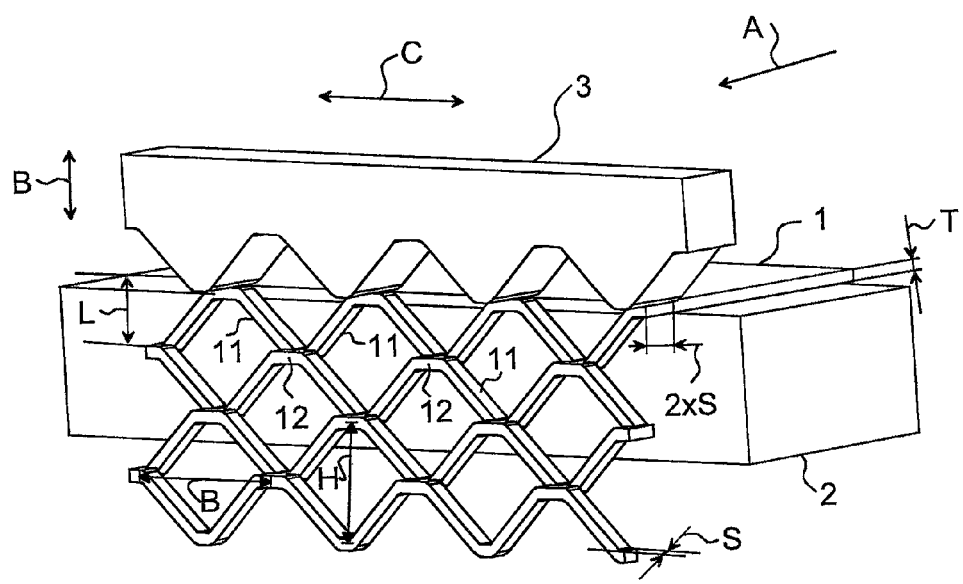
FIG. 1 is a schematic view in perspective representation, illustrating production of a network structure of expanded metal for a visor according to one embodiment of the invention.

Illustrative embodiments of the invention are described below with reference to the figures.

The production of a network structure of expanded metal for a visor is illustrated schematically in FIG. 1. A plate 1 of stainless steel and having the plate thickness T is placed in a metal-cutting machine which comprises a feed table having a support 2 and a toothed punching tool 3. The plate 1 is advanced step by step in a feed direction A which is parallel with the extension plane of the plate. In each feed step, the plate is advanced by a certain step width S, so that a corresponding section of the plate projects beyond the perpendicular edge of the support. After each feed step, a punch stroke is executed according to the following description. The toothed punching tool 3 is guided down towards the plate portion placed beyond the support, in a direction B which is perpendicular to the extension plane of the plate 1. The tool 3 comes into contact with the top side of the plate 1 and thereafter punches down farther a section L, which constitutes half the mesh height H of the finished network structure. The plate is hereupon cut with the formation of slots along the edge of the support 2. During continued downward movement of the punching tool, the plate strands located outside the slots are stretched such that they form integrated wire portions 11 which at their ends are bound together in connecting portions 12. Once the tool in this way, while cutting and stretching a row of wire portions 11, has punched down a row of connecting portions 12 over the section L, the tool 3 is guided back up to its starting position above the plate 1. During the following advancement step of the plate 1, the tool is displaced in the lateral direction C by a distance corresponding to half the pitch length between the teeth of the tool and half the mesh width B of the finished network structure. After this, a new punch stroke is executed, so that a new row of stretched wire portions 11 and connecting portions 12 is formed. After this, the tool is returned in the lateral direction C to the first position.

In this way, a generally stair-shaped integrated network structure having wire portions 11 and connecting portions 12 is formed, in which each connecting portion 12 binds together the respective ends of four wire portions 11.

In FIGS. 2A-D is illustrated a network structure formed in the above-described manner and belonging to a visor according to a first embodiment of the invention. In the production of the network structure shown in FIGS. 2A-D, the plate thickness T has been chosen at 0.30 mm and the step width S (see FIG. 1) has been chosen to be around 70% of the plate thickness T. The network structure comprises wire portions 111 and connecting portions 112. In FIG. 2C is shown a section along the line C-C in FIG. 2B. Since the section C-C is not taken perpendicular to the longitudinal direction of the wire portions, FIG. 2C illustrates a section which is not a perpendicular cross section through the wire portions. In FIG. 2C, the thickness of the network structure for use in a visor is further illustrated with dashed lines 113, 114. The lines 113, 114 also define the general extension plane of the network structure.

As can be seen from FIG. 2C, the section through the wire portions 111 has a rectangular shape. As a result of the above-described production method, two first opposite sides 111A of the section through the wire portions 111 have a first, lesser angle to the extension plane 113 and 114 of the network structure. The two second, mutually opposing sides 111B perpendicular to the first sides have a second, greater angle to the extension plane 113 and 114. In FIG. 2C are represented the first sides with lesser angle to the extension plane of the sides 111A and the second sides with greater angle to the extension plane of the sides 111B. Since that section through the wire portions 111 which is shown in FIG. 2C is not a perpendicular cross section of the wire portions, the sides 111A shown in FIG. 2C are somewhat longer than the corresponding first sides of the actual perpendicular cross section through the wire portions. The length of the first sides of the actual cross section of the wire portions is corresponded to by the plate thickness. The second sides 111B shown in the figures wholly correspond to the second sides of the actual cross section of the wire portions. The length of these second sides 111B is corresponded to by the step width S in the production of the network structure.

Since the network structure shown in FIG. 2C is produced with a step width S which is around 70% of the plate thickness T, the first sides 111A, with lesser angle to the extension plane 113 and 114, constitute long sides of the cross section. The second sides 111B, with the greater angle to the extension plane, constitute short sides of the actual cross section. By virtue of this configuration of the wire portions 111 of the network structure belonging to the visor, the Venetian blind effect which is found in the previously known visor having a network structure of expanded metal, is substantially reduced.

FIG. 2D constitutes a section along the line D-D in FIG. 2C and illustrates the cross section through the connecting portions 112. Since the line D-D extends perpendicular to the longitudinal direction of the connecting portions 112, FIG. 2D shows the actual cross sections through the connecting portions 112. In FIG. 2D also, the thickness of the network structure is represented by the dashed lines 113 and 114, which lines also define the general extension plane of the network structure. The cross section of the connecting portions 112 has mutually opposing first sides 112A, which have a first, lesser angle to the extension plane 113 and 114, and second mutually opposing sides 112B, perpendicular to the first sides, which have a second, greater angle to the extension plane 113 and 114. The length of the first sides 112A is corresponded to by the plate thickness T, and the length of the second sides 112B is corresponded to by double the step width S. The cross sections of the connecting portions thus have a rectangular shape having long sides which are somewhat longer than the short sides. The short sides 112A have a lesser angle to the extension plane 113 and 114 of the network structure than do the long sides 112B.

In FIGS. 2A-2D, the network structure is shown in the form which it has directly after the production stage illustrated schematically in FIG. 1. In one embodiment of the visor according to the invention, the network structure is utilized directly in this form in the visor. In another embodiment, the network structure, prior to use in a visor, undergoes a calendering process, in which the network structure passes between calender rolls. In this calendering process, the orientation of the connecting portions will first of all be affected. With that embodiment of the connecting portions 112 which is illustrated in FIG. 2D, the calendering will bring about a rotation of the connecting portions 112, so that the long sides of their cross sections are straightened up to a right or virtual right angle in relation to the extension plane 113 and 114 of the network structure. The light transmittance and the transparency for the network structure will hereby be further improved.

In further other embodiments, the network structure undergoes, alternatively to or in addition to the calendering process, a heat treatment for achieving relief of the material stresses which occur in the network structure, at the production stage shown in FIG. 1. Apart from the fact that such a heat treatment makes the network structure easier to handle, it also causes the surfaces of the network structure to become darker and matter, which prevents the formation of light reflections.

In FIGS. 3A-D, a network structure belonging to a visor according to a further embodiment of the invention is illustrated. In this embodiment, the network structure is formed by the method illustrated schematically in FIG. 1, in which the step width S is chosen at around 55% of the plate thickness. The network structure has wire portions 211, which are connected to the connecting portions 212. In FIGS. 3C and 3D, the thickness of the network structure is illustrated with the dashed lines 213, 214, which dashed lines also define the general extension plane of the network structure. The wire portions 211 have cross sections having short sides 211B which are substantially shorter than the long sides of the cross section, which long sides are somewhat shorter than the sides 211A shown in FIG. 3C. In FIG. 3D is shown a cross section through the connecting portions. In these cross sections, the sides 212B which have the greater angle to the extension plane 213 and 214 of the network structure are approximately equal in length to the sides 212A which have the lesser angle to the extension plane 213 and 214 of the network structure. The cross sections of the connecting portions 212 hence have a virtually square cross section.

The network structure shown in FIGS. 3A-D can in certain applications be used directly in a visor, or can, as described above, first undergo a calendering process and/or a heat treatment.

Above, illustrative embodiments of the invention have been described. It will be appreciated, however, that the invention is not limited to the above-described embodiments, but can be freely varied within the scope of the following patent claims.

The invention claimed is:

1. A visor comprising:
a network structure formed of expanded metal, wherein the network structure has a general extension plane and is formed of wire portions and connecting portions, the wire portions having respective ends thereof being joined in each connecting portion, and wherein the wire portions have substantially rectangular cross sections having long sides and short sides, and the wire portions are arranged such that the long sides of the cross sections have a lesser angle to the general extension plane of the network structure than the short sides, wherein adjacent ends of the wire portions are stacked to overlap one another and form the connecting portions and the short sides of the cross sections of the wire portions have a first length (S) and the long sides have a second length (T), and the connecting portions have opposing short sides and opposing long sides, the opposing short sides having a third length equal to the second length (T) of the long sides of the cross sections of the wire portions and having a lesser angle to the general extension plane than the opposing long sides, and the opposing long sides having a fourth length (2S) that is twice the first length (S) of the short sides of the cross sections of the wire portions, wherein the second length (T) is approximately 0.3 mm and the first length (S) is approximately 70% of the second length (T).

2. A visor according to claim 1, wherein the network structure is formed of stainless steel.

3. A visor according to claim 1, wherein the network structure is calendered.

4. A visor according to claim 1, wherein the network structure is heat-treated.

5. A visor according to claim 1, wherein the network structure is formed of annealed stainless steel.

6. A visor according to claim 1, wherein the substantially rectangular cross section is perpendicular to the general extension plane.

* * * * *